United States Patent [19]

Newmuis

[11] Patent Number: 4,754,487
[45] Date of Patent: Jun. 28, 1988

[54] PICTURE STORAGE AND RETRIEVAL SYSTEM FOR VARIOUS LIMITED STORAGE MEDIUMS

[75] Inventor: Lemuel Newmuis, Berlin, N.J.

[73] Assignee: Image Recall Systems, Inc., Whippany, N.J.

[21] Appl. No.: 886,906

[22] Filed: May 27, 1986

[51] Int. Cl.$^4$ .............................................. G06K 9/00
[52] U.S. Cl. .......................................... 382/2; 382/56
[58] Field of Search ...................................... 382/2, 56

[56] References Cited

U.S. PATENT DOCUMENTS 3,805,238  4/1974  Rothfjell ................................. 382/2
4,554,591 11/1985  Kee ...................................... 358/256

OTHER PUBLICATIONS

"The Recognition of Faces"; by Harmon; Scientific American; Nov. 1973, pp. 71–82, 136.
IBM Technical Disclosure Bulletin, vol. 21, No. 6, Nov. 1978, pp. 2515 and 2517.

*Primary Examiner*—James J. Groody
*Assistant Examiner*—Michael D. Parker
*Attorney, Agent, or Firm*—Antonelli, Terry & Wands

[57] ABSTRACT

A system for storing an image of an object to be identified and for retrieving the stored image of the object for displaying the same on a display screen. The system includes electronic scanner for scanning the object on a line-to-line basis to provide an analog signal for each line indicative of the information content of said object. The analog information is converted by a digitizer into pixels which define a matrix which matrix determines the information content for each line. A window area is generated which area encompasses a predetermined area within a larger display area. The window area is used to generate and to respond to a first set of digital information which information is derived from the matrix pixels. This first set of digital information is such that the window area contains a limited number of pixels plus a limited number of lines, each of which is generated when the window area is scanned. A critical identification area is defined by the apparatus which critical identification area is determined by the common characteristics areas associated with the object to be scanned. In an image of a person's face, the area consists of a "T" zone which encompasses the eyes, nose and mouth area. In this critical identification area, information is generated or employed which employs pixels that were skipped during the scanning of the window area. In this manner the critical identification area contains more detailed information to enable one to thereby authenticate the regenerated image from the first and second sets of digital data to thereby enable one to positively identify one person as compared to another person. The technique provides a video compression of such data whereby the resultant digital information is capable of being stored on a very limited medium such as a magnetic stripe associated with a credit card.

29 Claims, 5 Drawing Sheets

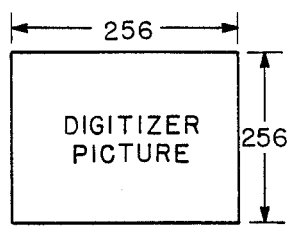
FIG. 3A
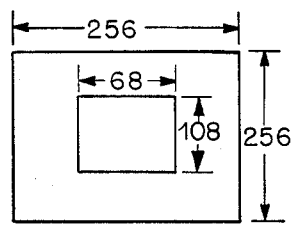
FIG. 3B
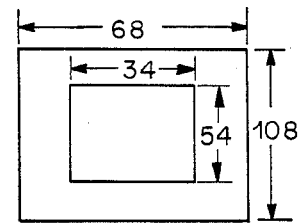
FIG. 3C
FIG. 4
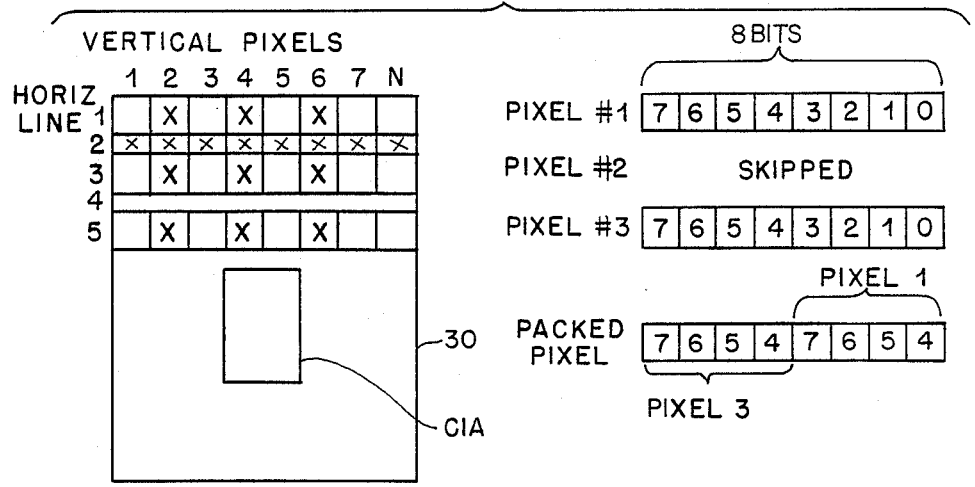
FIG. 5
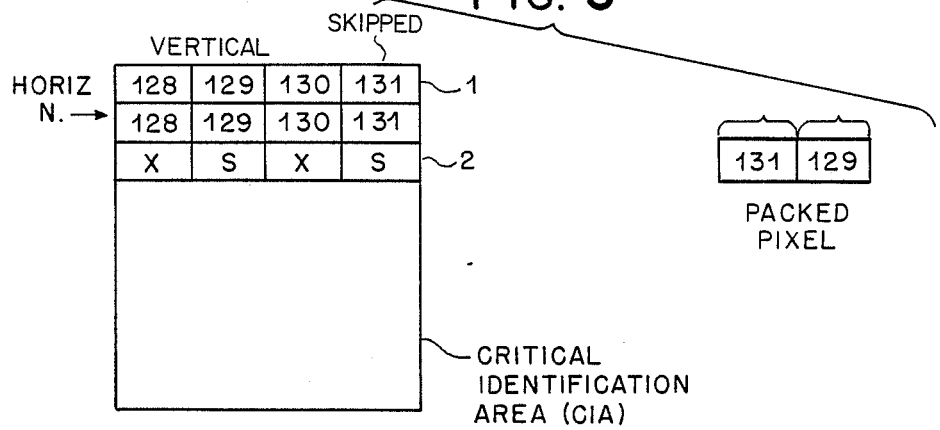

PICTURE STORAGE AND RETRIEVAL SYSTEM FOR VARIOUS LIMITED STORAGE MEDIUMS

BACKGROUND OF THE INVENTION

This invention relates to a system for storing image information indicative of an object to be identified and for retrieving and verifying such stored information to enable one to obtain a reconstructed image of the object.

In particular, the invention relates to the digital processing of information indicative of the major recognizable features of an object such as the face of a person. This information is then digitized and stored. The technique utilizes a unique compression scheme which enables one to obtain an accurate representation of the face of a person or other object by accessing a critical identification area which is determined according to the characteristics of the particular object. Then by utilizing a high resolution processing sequence within the critical identification area, one is enabled to substantially and significantly reduce the total amount of storage required. Thus, a final representation of a pictorial view of a person's face can be digitally stored on storage mediums having very limited storage capacity such as a magnetic tape or other similar mediums which are associated with credit cards and so on.

Essentially, the prior art is replete with various systems which attempt to authenticate or provide visual data to enable the recognition and identification of persons or person's signatures. Typically, such systems employ the use of a computer and memory or other data processing systems to process various data which has been digitized and stored in a memory. The data indicative of the object is then retrieved and processed so that a visual indication of a signature or a person's face is presented as a display on a television monitor or other suitable display terminal. Such systems as indicated have been investigated in the prior art and there are many techniques associated with such systems which essentially involve compression of such data in order to accommodate limited storage space and to reduce the number of bytes necessary to provide an accurate visual representation of a person or a person's signature. Examples of such prior art may be had by referring to the following patents.

U.S. Pat. No. 3,718,908 to R. W. Bloomstein issued on Feb. 27, 1973 and is entitled Signature Storage and Retrieval System. This patent optically scans a signature which is then encoded by means of a digital encoder. The patent describes the use of a digital computer which stores digital information relating to the signature. The digital information can then be retrieved, decoded by means of a decoder and then displayed on a CRT screen such as a television monitor for comparison of the signature with the actual person's signature.

U.S. Pat. No. 4,020,463 to D. P. Hemel issued on Apr. 26, 1977 and entitled Apparatus and Method for Storage and Retrieval of Image Patterns. This patent shows a system whereby a signature or other image is optically scanned to generate digital signals for storage in a matrix. These signals represent black and white cells which define the line signature and are initially processed by tracing the image boundary. This processing, which is done electronically, thins or peels off the data by the use of an algorithm that evaluates black areas of the image matrix for conversion into white area digital signals. The patent employs a form of data compression and this compression continues until the line signature or line image is composed of a single area thickness.

Other patents such as U.S. Pat. No. 4,101,958 to D. A. Domiki issued on July 18, 1978 entitled Terminal Display and Storage Medium. The patent relates to a system wherein a video camera scans an image which image is located within a particular area. The image is digitized and stored and then can be retrieved and displayed on a CRT or television monitor. The general nature of the system utilizes a data compression technique whereby only those relevant bits that relate to a given character serve to designate the number of spaces as recorded. Hence, the appropriate number of blanks are recorded as a single character formed which indicates a number of blanks thereby compressing character bits. After storage, the operator at the terminal can retrieve and display the signature or image that has been stored.

Other patents such as U.S. Pat. No. 4,344,135 to H. D. Crane issued on Aug. 10, 1982 entitled Dynamic Creation of Signatures as well as U.S. Pat. No. 4,364,024 to K. Paetsch issued on Dec. 14, 1982 entitled Signature Presentation Method and Apparatus, involve typical systems.

Patents like the above also show systems which attempt to verify a signature by taking the requisite bits of a signature and so on, and utilizing various compression techniques, store such bits as digital data in a memory. The bits as stored are indicative of a signature or an image and are then retrieved and displayed on a cathode ray tube.

As one can ascertain, the above-noted patents are indicative of some of the type of prior art which attempt to verify a signature or the identity of a person by utilizing digital processing techniques to thereby store data in a memory which data is indicative of the image. This data can then be retrieved and displayed on a cathode ray tube or other display device to enable a party to either recognize or authenticate the signature or recognize or authenticate the person who is to be identified.

In any event, a significant problem which was encountered in such prior art systems is the ability to store the necessary amount of bits and to thus provide an accurate replica of the image to the identified. Briefly speaking, the prior art techniques did not lend themselves to enable one to use a relatively limited storage medium and to use such a medium to store enough digital data whereby the data as retrieved would enable one to make a positive identification of the person or object. As is well known, a typical credit card employing a magnetic stripe is a limited storage medium. Hence, in order to store data indicative of an accurate visual representation of a person's face the typical magnetic storage tape associated with a credit card does not accommodate the number of bits which were required by most prior art systems. In this manner, one could not store on a limited storage medium such as a magnetic strip or tap associated with a credit card the requisite number of bits to enable one to provide an accurate representation of a person's face or other complicated image. While prior art techniques recognize the need for data compression, such compression schemes do not lend themselves to use limited storage while providing an accurate representation of the object to be identified or authenticated.

Compression techniques that are presently used required that images be reconstructed or decompressed before transmission to the display device. Many such systems utilize a significantly wide transmission bandwidth and require a large amount of memory to accurately produce an image which image can be utilized to identity or otherwise authenticate the actual object. Essentially, present day compression techniques are utilized on textured images or images which have significant thickness to individual parts and with compression ratios in the range of 3 to 1 to 10 to 1, depending on the particular image or technique. There are many, many different techniques which involve compression of data which have been employed by the prior art to attempt to reduce the amount of storage necessary in order to provide an accurate representation of an image or an object which is to be authenticated.

It is also well known that a major use of accurate authentication in today's society involves the credit card industry. It is therefore apparent that it would be extremely desirable to enable one to store on a magnetic stripe associated with a credit card digital data which is indicative of the identity of the person to whom the card is assigned to. In this manner, one would desire to be able to store an accurate representation of the actual portrait of the person who owns the card to enable identification of that person at a remote terminal such as a bank terminal, a credit card terminal, or as a means for identifying a person for access to a secured premises.

Essentially, as one can ascertain, there are a multiplicity of uses for such a system whereby a video image or other representation of a person can be produced by means of a credit card carried by that person. The prior art was cognizant of the need for such a device and employed many different schemes such as holographic cards, digital cards with complicated data storage formats, cards employing microprocessing circuitry and individual memories and so on. In any event, it is indicated that based on such prior art techniques, there does not exist a system which is capable of storing on a conventional magnetic stripe of a conventional credit card digital data indicative of a accurate portrait or representation of a person to be authenticated or identified.

It is therefore an object of the present invention to provide apparatus and techniques for verifying the authenticity of an object using various limited storage mediums such as a magnetic stripe card similar to a credit card.

It is a further object of this system to provide a digital storage technique which employs compression to enable one to achieve an accurate representation of an object utilizing a minimum number of bits to thereby enable one to store accurate representations of the object in a minimum amount of space.

BRIEF DESCRIPTION OF THE INVENTION

Essentially, the system utilizes an electronic picture which is taken of the object. Because of the limited and variable storage capabilities presented by such mediums as described above, the system utilizes a variety of bit eliminating processes to extract unnecessary data to allow for a high resolution image to be constructed to fit the storage capacity of the device being utilized. To accomplish this, the electronic picture is put into digital form to enable alignment, brightness, contrast and focusing. The alignment, brightness, contrast and focusing process continues until an acceptable picture is verified. After acceptance, the picture is altered to fit both the display size needed for the application and the bit storage capacity of the storage medium used. The resultant digital data is then stored on the magnetic stripe or the suitable medium and can thereafter be retrieved and utilized to provide an accurate representation of the object indicative of the stored data.

As indicated above, the retrieval system can be used for many, many applications such as positive identification of a person or for analysis using very limited storage mediums. It is of course understood that in addition to a magnetic stripe card which is a preferable form of storage medium in regard to this invention, other storage mediums may include various other types of cards, all of which can be employed with a magnetic stripe or other memory devices of limited storage capacity.

BRIEF DESCRIPTION OF FIGURES

FIGS. 3A-3C are a series of additional diagrams explaining the compression scheme according to this invention.

FIG. 4 is a series of schematic diagrams describing the video compression technique using a window area as employed with this invention.

FIG. 5 is a schematic diagram showing the compression as implemented in the critical identification area.

DETAILED DESCRIPTION OF FIGURES

Figure 1:
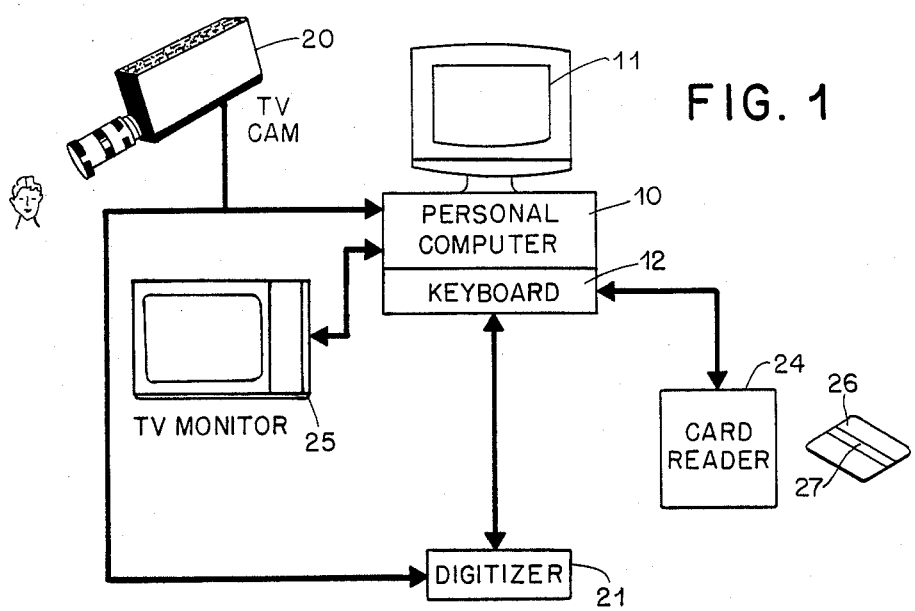
FIG. 1 is a simple block diagram depicting a picture and storage retrieval system for various limited storage mediums according to this invention.

Referring to FIG. 1, there is shown a simple block diagram of the system to be described in regard to this application. The system incldues a personal computer or microprocessor 10 which may normally be associated with a display terminal 11 and which conventionally includes a keyboard 12. Such personal computers are well known and many examples exist in prior art such as the IBM PC, and the IBM AT or various other computers made by many manufacturers which essentially are compatible with or capable of producing similar results to the above-noted computers. At the onset, it is understood that much of the system to be described is implemented in terms of software which is processed by the computer to enable one to provide the various objects of this invention. In any event, it should be apparent to those skilled in the art that an actual hardware system can be employed as well as will be further described.

Essentially, the computer 10 is coupled to various devices to enable the system to operate. There is shown a television camera 20. The television camera 20 is a conventional component available from many manufacturers and is utilized to provide an electronic picture of an object. While a television camera is shown, it is known that there are many other types of devices which can be utilized to respond to various conditions of ambient light to thereby produce an electronic or analog output indicative of the image of an object. Such devices, as television cameras or optical scanners, all function accordingly. The television camera 20 is utilized to generate a video signal containing the image of a particular televised object. The operation of television cameras and the format for displaying images generated by television cameras is well known in the art and is not in fact considered to be part of this invention. It is also understood as indicated above, that many different types of devices can be employed for responding to an image of an object. It is also understood that a main aspect of this invention utilizes and is concerned with producing accurate reprsentations of images of persons, namely, the person's face. The image of the person's face is, as indicated, digitized and stored and such data can be stored on typical limited storage mediums such as a magnetic stripe. Thereafter, the digital data stored on the stripe is retrieved to produce on a television monitor a very close replica of the image to enable one when viewing the image to identify the person directly. Thus, a major object of the invention is to store digital data on a medium with limited storage capacity as afforded by a magnetic stripe card. In any event, it would be understood that various different types of storage mediums can be employed as well as the fact that various different types of objects can also be identified using the teachings of the system and techniques.

The television camera 20 is coupled to a digitizer 21 which is also coupled to the personal computer. the function of the digitizer is to produce a digitized output of the electronic or analog image provided by the television camera. This digitized output is then operated on to produce digital data which can be stored or otherwise impressed on a magnetic stripe associated with a credit card. The output of the digitizer is shown directly coupled to the computer 10 through a bidirectional bus. It is also understood at the onset that the computer 20 can communicate with the digitizer and in turn, the digitizer can communicate with the computer 20. Also shown coupled to the computer is a card reader/writer device 24 and shown adjacent to the card reader/writer device 24 is a credit card 26 having a magnetic stripe 28 thereon. Such credit cards are well known and exist in the prior art. Essentially, such credit cards have been utilized to store various graphic information indicative of account numbers and so on. As is well known, the number of bytes afforded by the storage medium on the card is relatively low and based on prior art video or digital compression techniques, one was not able to store data on such a magnetic stripe which was truly indicative of an accurate image of the rightful holder of such a card.

Also shown coupled to the personal computer is a television monitor 25. The monitor 25 is employed to provide a visual indication of the digital data on the credit card and to further provide means for formulating the picture so that it can be accepted and then stored according to the techniques to be described in this system.

In summation, the function of the system is to verify the authenticity of an object such as the face of a person. The data generated by the system is stored on a magnetic stripe which can be employed as the storage medium. In order to generate such data, the television camera 20 is utilized to take an electronic picture of the subject to whom the credit card 26 is assigned to. The electronic picture is put into digital form to enable alignment, brightness, contrast and focusing. Thus, in employing the system, the television monitor 25 first displays a window or area which may be centrally or otherwise suitably located on the television screen. This area defines a window for the image which is being taken of the particular person. The image of the person then appears within the window generated by the apparatus. The operator then reviews the picture in accordance to light, resolution, focusing and so on and when he sees an acceptable picture, presses a key on the computer keyboard which may be an enter key or any other key to thereby capture the picture as accepted by the operator. As will be explained, the electronic picture as present on the screen in derived from digital information as processed by the digitizer 21 and as further operated on by the system apparatus. When an acceptable picture is viewed by the operator, that picture has been converted to digital data according to the system operating techniques. The picture as accepted by the operator is indicative of digital data which is then impressed upon the magnetic stripe 27 associated with the credit card 26 by the card reader/writer device 24. The credit card having the stored picture can then be used to reconstruct the picture and display the same on television monitor or display 25. The picture storage and retrieval system for use with a credit card magnetic stripe can re-display pictures for positive identification and analysis. Under control of the program or software which is placed in ROM of the personal computer, the digitizer 24 operates to first cause the window to appear on the screen of the video monitor 25. The purpose of the window is to enable the camera operator to view the image taken by the television camera within the window. The digitizer 21 then commences operation and continuously captures and digitizes picture frames until the camera operator approves of the digitized picture as viewed. At this point in time, he presses a suitable key on the keyboard 12 which then captures the picture in computer memory. The computer is then commanded to transmit the digital data as stored in computer memory to the magnetic stripe 27 associated with the credit card via the card reader/writer device 24. Alternatively, as one can understand when a credit card as credit card 26 is inserted into the card reader 24, the digital information stored on the credit card is then read into computer memory and processed so that the information is then displayed on the television monitor within the same window area. The data stored gives the user an accurate representation of the object or person's picture as originally accepted and then stored on the credit card via the magnetic stripe 27.

As indicated above, wide variety of techniques exist for processing pictorial information by the use of a computer. These techniques are collectively referred to as image processing or picture processing. Information to be processed is usually input to the computer by sampling an analog to digital conversion of video signals obtained from some kind of two-dimensional scanning device as for example, a television camera, facsimile scanner and so on. Thus, at least initially, this information is in the form of a large array in the case of ordinary television which is about 500×500 in which each element is a number, typically 8 bits in length representing the brightness of a small region in the scanned image or a set of such numbers representing its color. The elements of a digitized picture are sometimes referred to as pixels or pels and their values in the non-color case are called gray levels. The key distinction between image processing and computer graphics is that the latter does not deal with input pictures in an array form although it may construct images from input sets of coordinate data.

Most of the classes of pictures encountered in practice are redundant in the sense of information theory and can be compressed to some extent without the loss of information using efficient encoding techniques. Thus, if one does not require that there be no loss of information, one can achieve higher degrees of compression if the picture is approximated by another picture having a lower information content which can then be further compressed. As indicated, the prior art was cognizant of these techniques. One very common class of picture compression techniques takes differences between successive pixels in time or space. Since such pixels are usually interdependent, these differences are more redundant than the original values. Another approach employed in the prior art employs transforms which are, for example, Fourier transforms which can be roughly approximated and still yield acceptable reconstructed pictures. Applications of image compression include television, facsimile and various other types of narrow band transmission systems.

Figure 2A:
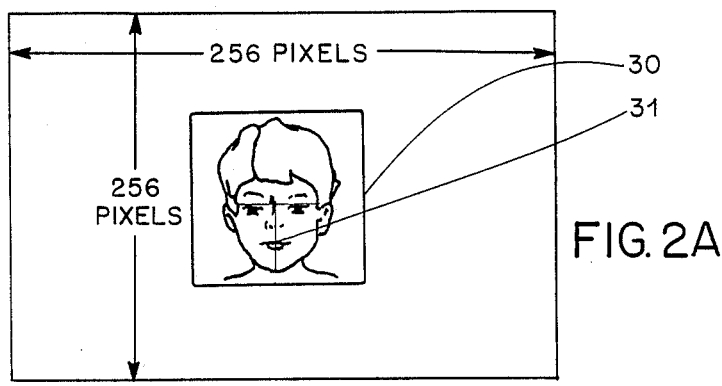
FIGS. 2A and 2B are a series of diagrams necessary to explain the operation of the invention.

Referring to FIG. 2A, there is shown a simple diagram depicting the screen of the television monitor 25. As will be explained, the system operates in two modes. One mode is to generate an acceptable video picture which is to be then stored on the magnetic stripe or other storage medium. In the second mode, the data that is stored is then processed by the system to thereby display the image on the television monitor.

Referring to FIG. 2A as will be explained, the system first produces the window 30 which is the area in which the operator of system is instructed to direct his attention to. At the same time the window is provided, a critical identification area 31 (CIA) is also displayed on the video monitor display. As will be explained, there are many parts of the picture which are redundant while there are other parts of the picture which are not completely necessary to accurately or truly identify the particular object. In the case of a human face, there is an area which is truly important to enable accurate identification of the subject. This area is referred to as the critical identification area (CIA) or critical identification zone. In the case of the human face, the zone as represented by numeral 31 is indicative of a T-shaped zone. Thus, the zone covers the eyes of the person, the nose of the person and the mouth as shown for example in FIG. 2A. The operator of the camera is then instructed to align the T with the image of the person's face in the manner shown in FIG. 2A.

Figure 2B:
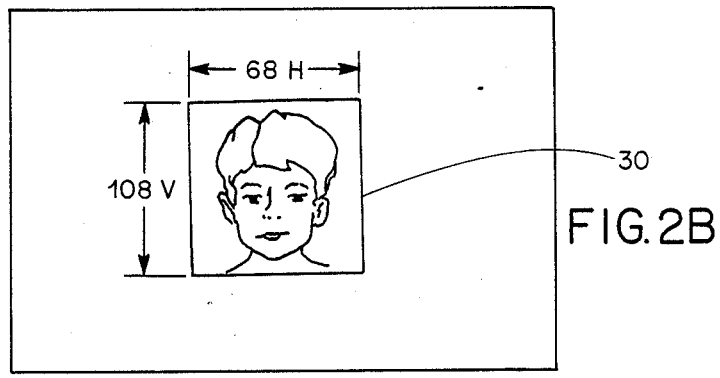

As will be explained, in the critical identification area or zone 31 the apparatus provides a detailed byte or digital representation of that area while in adjacent areas such as for example the hairline or forehead of the individual, the data is stored in lesser detail and essentially those areas are represented by a less detailed portrayal of the individual. Typically, a picture as evidenced by a typical television frame consists of 256 pixels in the horizontal direction and 256 pixels in the vertical direction. The term pixel has been defined above. The window area 30 within which the desired image is presented is representatiave of 68 pixels in the horizontal direction and 108 vertical lines in the vertical direction. Thus as one can ascertain, the system first produces the window 30 ignoring 188 pixels in a horizontal direction. In this manner if the picture were accurately centered, there would be 94 pixels to the left of the box 30 and 94 pixels to the right of the area 30. It is of course understood that the window can be located any place on the television screen but for present purposes, the area 30 indicative of the picture area is shown at the center of the television screen. Thus, as shown in FIGS. 2A and 2B, the outer alignment window 30 instructs the camera operator as to the position of the person's face. The T area 31 which also appears within the area 30, instructs the operator generally where to position the subject's eyes, nose and mouth. It is of course understood that dimensions between different person's eyes as well as the dimensions of typical individual's nose and mouth all vary. Hence, the T zone 31 is typically formulated to accommodate for all such variations. While the term T zone is utilized, it is of course understood that one really not need to employ a T zone area, but can employ for example a plurality of areas as a left and a right box to accommodate the person's eyes, a central box to accommodate the person's nose and a smaller box to accommodate the mouth of the person. The re-displayed image which appears in FIG. 2B essentially is a accurate replica of the image of FIG. 2A as accepted by the operator. It will be understood that the image of FIG. 2A is constantly being generated by the processing techniques utilized by the system and the electronic image produced by the television camera is constantly being digitized to produce an image on the televison monitor which is viewed by the television camera operator. When the television camera operator views an acceptable correlation between the image on the television monitor and the subject that is being television, he then presses a capture button which then stores the exact image in computer memory. This stored digital data is then impressed upon the magnetic stripe of the credit card or upon another storage medium to thereby store data which can be converted to an accurate image of the subject or object.

The system to be described operates according to the following principles. Within the area of concern which is essentially the outer alignment window 30, every other pixel is skipped as is every other horizontal line which therefore produces a resulting 34 H×54 V picture. When the picture is redisplayed, each original 8 bit pixel is compressed into four bit pixels to represent every other pixel and every other scan line that were skipped. During redisplay, each 4 bit pixel in the window area is repeated below and to the right. The two below are to fill in the skipped line and the one to the right is to fill in the skipped pixel. In the critical identification area, skipped pixels were responded to and thus the 4 bit value of the skpped pixel is now present to the right of the 4 bit value retrieved during the window scan. Thus, in the critical identification area each line within the area has a 4 bit consecutive values with no skipped or missing pixels. This information is now replicated for the unscanned line below in the critical identification area. The critical identification area 31 is then overlaid with the window picture as above described to produce a detailed image of the eyes, nose and mouth area of the subject matter. Thus as will be explained, additional bits are retrieved in the critical identification are to therefore accurately represent the eyes, nose and mouth area of the subject.

The initial digitized picture which consists of 256 vertical pixels by 256 horizontal scan lines includes the input picture window as manifested by the area 30 so that it consists of 68 vertical pixels ×108 scan lines. This is a variable window and can be positioned by the operator to focus on the specific subject. The input picture window is finally compressed to the packed picture window state by removing every other pixel horizontally and every other line vertically. The final form of 34 pixels ×54 horizontal scan lines is the resultant picture. This aspect of the invention is depicted in FIG. 3A, B and C.

The original 8 bits pixel definition describing 256 shades of gray is compressed to four bits/pixels which define 16 shade of gray. It is of course understood that other picture digitizers can be used. For example, 512×512 instead of 256×256 and the technique described can be employed with such other types of systems.

Referring to FIGS. 3A, 3B and 3C, there is again shown in diagrammatic form the particular nature of the technique employed. FIG. 3A shows the initial digitizer picture which as indicated consists of 256 horizontal pixels ×256 horizontal scan lines. Thus, each horizontal line contains 256 pixels across the length. In regard to this, each initial pixel characterstic can be indicated by 8 bits which is equivalent to 256 shades of gray. In any event, referring to FIG. 3B, the digitizer input picture window is depicted. In the digitizer picture window, there are 68 pixels ×108 horizontal scan lines which defines the area in which the photograph or electronic picture of the person is displayed. FIG. 3C shows the picture window. As one can see, essentially the 68 pixels and the 108 horizontal scan lines is further reduced to a pixel density which consists essentially of 34 pixels by 54 horizontal scan lines. The final pixel characteristics is the internally packed picture window consists of four bits for each pixel which essentially represent 16 shades of gray.

In any event, the initial digitized picture as indicated in FIG. 3A is 256 pixels by 256 horizontal scan lines. The input picture window shown in FIG. 3B of 68 pixels ×108 scan lines is displayed within the 256×256 picture. This is of course a variable window and can be positioned by the operator to focus on the specific subject. The input picture window is finally compressed as indicated in FIG. 3C to the packed picture window state by removing every other pixel and every other line down. The final form of 34 vertical pixels ×54 horizontal scan lines is thus obtained as indicated in FIG. 3C.

In any event as will be explained, in the critical identification area, increased pixel storage is implemented to therefore enable one to obtain much greater resolution in the critical identification area, thus resulting in a stored image which is a truly accurate representation of the person's face as compared to other compression techniques. Essentially based on the above-noted criterion, one can now form a number of bytes completely indicative of a person's picture and store those bytes on a very limited storage medium such as a magnetic stripe associated with a credit card.

Referring to FIG. 4, there is shown in diagrammatic view a representation of what is occurring during a picture scan. Essentially as shown in FIG. 4, the line pixels are designated strictly for convenience as 1-N while the horizontal lines are designated 1, 2, 3, 4, 5 and so on also up to N. It is on course understood that the area of concern is represented by the outline pattern which is the window 30 generated on the television monitor.

As can be seen from FIG. 4, every other pixel is skipped. Thus, the system responds to produce 8 bits regarding pixel no. 1 in the vertical direction, pixel no. 2 is skipped, the system then responds to produce 8 bits for pixel no. 3, pixel no. 4 is skipped and the system then responds to produce 8 bits for pixel no. 5, pixel no. 6 is skipped and so on. This process continues. In regard to the horizontal lines, the system operates to provide the first horizontal line, skips the second horizontal line, produces the third horizontal line, skips the fourth horizontal line and so on. As one can ascertain from FIG. 4, the x's indicate which of the pixels are skipped. To the right of the matrix designated by numeral 30 is an indication of the pixel characteristics which consist of 8 bits for each pixel as pixel no. 1, pixel no. 3 and so on. Essentially, the system operates as follows. The 8 bits of pixel no. 1 ae treated so that bits 0, 1, 2 and 3 are cleared and only the four upper bits as bits 4, 5, 6 and 7 are saved. In pixel no. 3, the same process occurs whereby bits 0, 1, 2 and 3 are cleared and bits 4, 5, 6 and 7 are saved. The four upper bits of pixel no. 1 are then packed to be four lower bits in the packed pixel while the four upper bits of pixel no. 3 are packed to form the four upper bits in the packed pixel. Thus, the packed pixel which consists of 8 bits has the lower four bits indicative of the information content of pixel no. 1 while the upper four bits are indicative of the information content of pixel no. 3. This process continues whereby as one can ascertain, the next packed pixel consists of four bits from pixel no. 5 which would be packed as the lower bits in a packed pixel with four bits from pixel no. 7 as the higher bits and so on. Thus, according to the bit packing process just described, the method and technique operate to place two pixels in regard to the four upper bits of each pixel into a single packet pixel which consists of 8 bits or one byte.

As seen from FIG. 4, a process also occurs throughout the critical identification area indicated by CIA on the diagram. It is understood that the critical identification area is preferably a T zone for a person's image as shown in the previous drawings but can be any zone or zones which encompass the major recognizable features of a particular object which is being scanned by the television camera. In the critical identification area, the same processing occurs, whereby lines and alternate pixels are skipped. This occurs during a first processing scan which is the window scan. During a second processing scan, the apparatus when scanning the critical identification area picks up those pixels which were skipped during the first processing scan. Thus for example, during the first scanning process and referring to FIG. 5, pixel 128 and pixel 130 would have been responded to. Pixel 129 and pixel 131 would have been skipped. During the scanning of the critical identification area, the system now produces 8 bit indications for each of the skipped pixels. For example, when scanning the critical identification area, the system will now produce an 8 bit number indicative of a previously skipped pixel as pixel 129 and another 8 bit number indicative of pixel 131 which was also skipped during the first scanning process. The pixels 129 and 131 are then combined as indicated above to form a packed pixel which consists of the upper four bits of pixel 129 and the upper four bits of pixel 131 to produce thereby another byte indicative of the information content in pixel 129 and 131. This occurs for all pixels in the critical identification zone or area which were previously skipped during the window scan. The skipped horizontal lines associated with the critical identification area are now filled in with the information content of the previous line. For example, as shown in FIG. 5, horizontal line N would have been a line that was skipped and the system would have responded to line 1 by producing values for pixels 128 and 130, would have skipped line N, would have then produced pixel values for line 2 as designated by the number X and would have skipped alternate pixels in line 2 as designated by the letter S.

In any event the system, when scanning the critical identification area now responds to skipped pixels as 129 and 131 and forms a packed pixel consisting of the information content of the formerly skipped pixels 129 and 131. The entire information which was formulated for line 1 is now inserted in line N so that there is no skipping of horizontal lines in the critical identification area, but the information obtained from a scanned horizontal line is repeated in the critical identification area for the next succeeding line. This technique substantially increases the resolution of the system. Thus, it allows one to accurately produce an image beyond that accomplished with other video compression techniques. Thus, according to this method, while alternate pixels are skipped during a first scan and alternate horizontal lines are also skipped during the first scan, during the scanning of the critical identification area, skipped pixels are responded to and are packed so that two skipped pixels are placed in one 8 bit storage location to produce a byte indicative of the skipped pixels. Thus, the entire information for one horizontal line is obtained as indicated in FIG. 5. This information is then repeated for the next horizontal line which also would have been a skipped line in the original scanning scheme. Thus as one can ascertain, during scanning of the critical identification area, the requisite information is now inserted into skipped pixel locations and into skipped horizontal lines. This thereby makes the entire resolution much greater in the critical identification area and accurately enables one to positively identify the subject.

To give one a better indication and understanding of what is occurring, reference is again made to FIG. 2A. In FIG. 2A, the critical identification area has been defined by the T 31. It is of course indicated that the T is indicative of one type of critical identification area and this particular area can be manifested by other suitable areas. It is also known for example that the critical identification area 31 as well as the window 30 would start in the vertical direction at a given pixel count and in the horizontal direction at a given line. It is noted that the window 30 can be positioned anywhere on the screen of the television monitor and all one has to know is where the window is to be positioned and hence identify both the window and the CIA by counting pixels as well as counting lines.

Figures 6, 7:
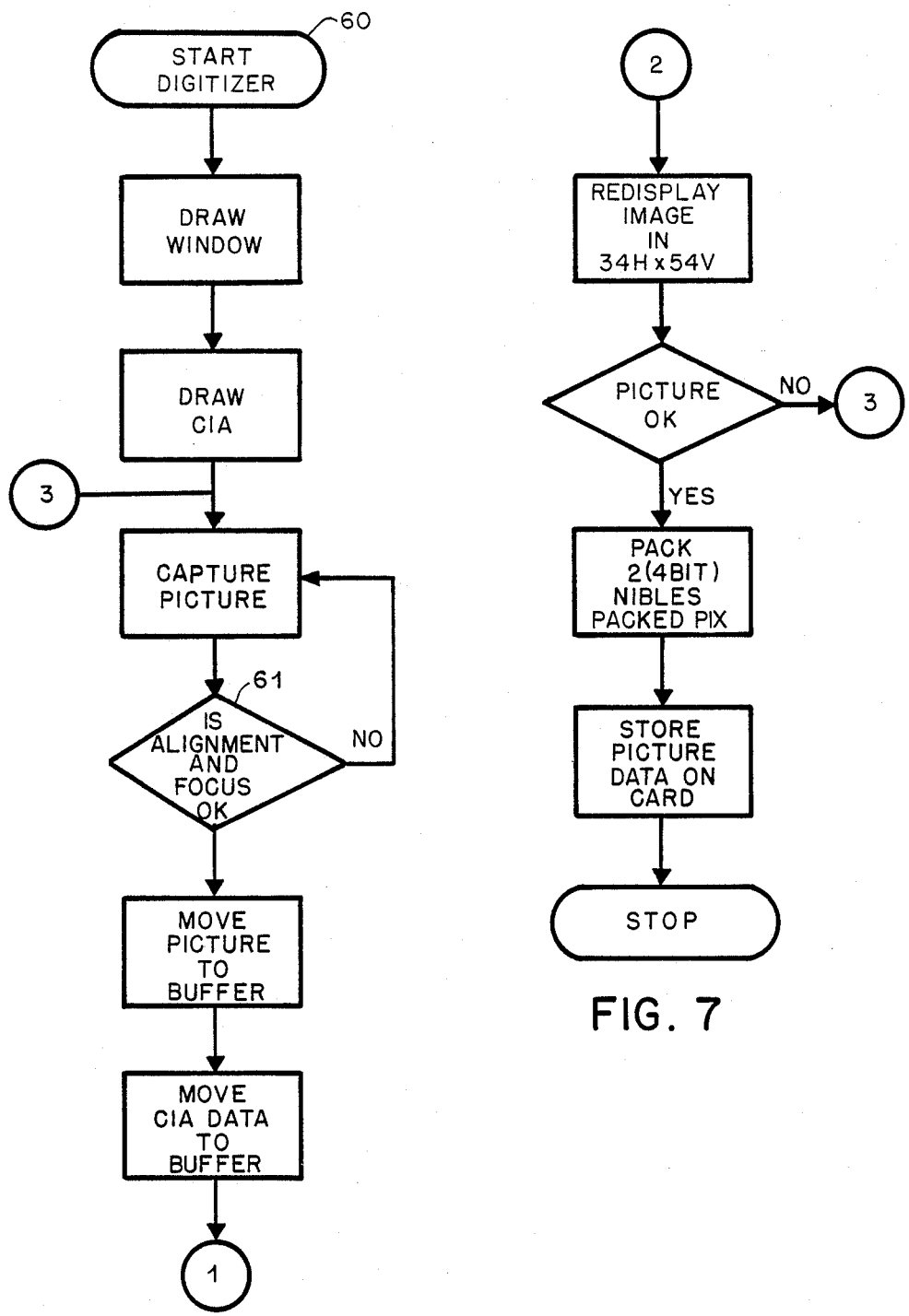
FIG. 6 is a simple flow chart explaining the generation of the window and critical identification areas.
FIG. 7 is a simple flow chart used in conjunction with FIG. 6 necessary to explain how a television image is accepted according to the principles of this invention.

Referring to FIGS. 6 and 7, there is shown simple flow charts depicting the various steps which are necessary to capture a picture and to impress the captured pictured on a typical magnetic stripe associated with a credit card. Essentially, as one can see from FIG. 6, the first step in the process indicated by module 60 is the start digitizer step. Essentially, the digitizer which is shown in basically an analog to digital converter. Such devices are well known and employed in digital video techniques. The conversion of a video signal into a digital signal employs an analog to digital converter in which the analog composite video signal is sampled at a high rate. This rate is typically equal to three times the chrominance subcarrier frequency in the case of color signals and the amplitude of each successive sample is adjusted or quantized to the upper or lower limit of the interval between the binary levels. The NTSC composite video color signal is typically quantized into 256 levels as above indicated where each pixel constitutes 8 bits of information. Each quantized sample amplitude is encoded by pulse code modulation into a binary 8 bit number and the succession of these numbers constitutes a bit stream that represents the video signal in digital form.

Essentially based on the high sampling rate, each television line is sampled a plurality of times to thereby generate 256 intervals for each line. Each of the 256 intervals as above defined is a pixel. Each pixel is manifested by 8 bits which therefore enable such a system to give 256 shades of gray or 256 gray levels. Essentially, the digitizer employed in this system is a conventional component and many examples of digitizers are well known in the art. The digitizer as shown in FIG. 1 has direct access to the television monitor via the computer and hence the output of the digitizer which is digital information is coupled through the computer to the television monitor.

Essentially, the digitizer is started and the program incorporated in the microcomputer is then instructed to cause the window 30 for example to be drawn on the face of the television monitor. After the window 30 is drawn, the microcomputer enables the image of the critical identification area to be drawn on the television monitor. Hence, the operator of the television camera during this mode now sees the window 30 on the television monitor together with the outline of the critical identification area to enable him to align the subject's eyes, nose and mouth areas as indicated above.

The next step is that the operator visualizes the picture and the picture is continuously being processed. As one can see from FIG. 7, the information which is the compressed data information is continuously being displayed so that the operator can see the same. When the operator sees an acceptable picture, he presses a button on the computer which essentially captures the picture in that the digital information which is being processed is now stored in the computer and hence the display of the captured picture is in fact the stored image. The operator looks at the display to determine whether the alignment and focus of the same is okay. This is depicted by the decision module 61 of FIG. 6. If it is not okay, then he continues to operate the camera in regard to focus and alignment as well as considering lighting techniques until he again sees a picture which he thinks will be acceptable. He then presses the same button on the computer to capture this picture. If the picture is acceptable, the entire digital contents of the picture which are stored in the computer are moved to a buffer. The critical identification area data which is indicative of the above mentioned T zone is also stored in the computer and this is representative of the picture.

As indicated, this picture essentially constitutes 34 pixels by 54 lines. What is meant by this is that what is stored is data indicative of 34 pixels or essentially the 34 vertical pixels with the number 54 representing the number of horizontal lines that are stored. Thus, the image which is essentially contained in 34 horizontal pixels by 54 lines is constantly being displayed. When the operator makes a determination that the picture is okay, he then captures the picture as indicated in FIG. 6. The information relating to that picture is packed as explained above, whereby the four upper bits of each adjacent pixel are combined to form a nibble or a packed pixel. These are then stored in the computer memory and are then emplaced on the magnetic stripe associated with the credit card via the card reader/writer. After this is done, the magnetic stripe associated with the credit card has a series of digital data impressed thereon. Each of the digital data is indicative of a packed pixel which therefore represents 8 bits, four of which are associated with alternate pixels to formulate the picture. The credit card also has stored thereon the information indicative of the critical identification area which as will be explained can then be retrieved from the credit card to produce a picture from the credit card indicative of the picture that the operator accepted in the first instance.

Figure 8:
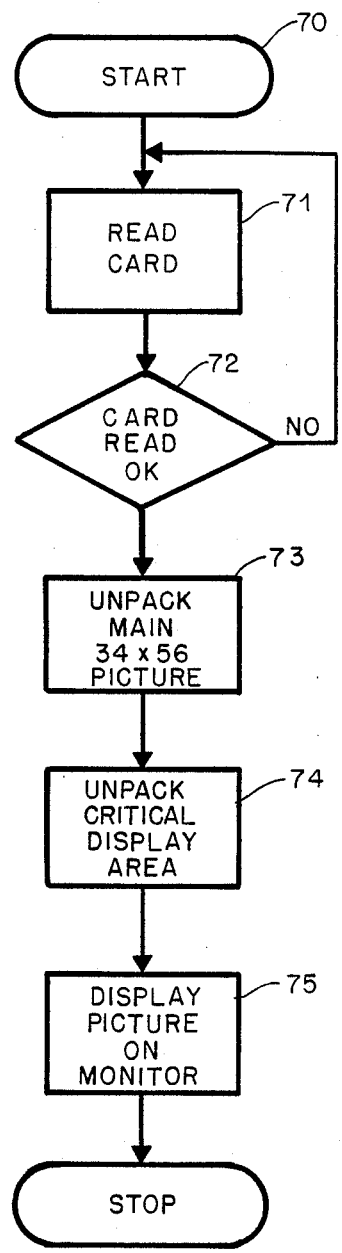
FIG. 8 is a simple flow chart showing the card reading procedure whereby digital data on a credit card can now be read and an electronic display of the individual be implemented.

Referring to FIG. 8, there is shown a simple flow diagram showing the reading of a credit card. Essentially, module 70 refers to the start of the program. The credit card is then introduced into a card reader as indicated by module 71 where the card is read. The information emanating from the card is checked in terms of bit content and polarity to determine if it is okay. This is all done by the computer. If the information is okay, then the digital information is unpacked according to the manner in which it was stored on the card. Thus, for example, the system utilizes 8 bit numbers to represent alternate pixels. This information is unpacked accordingly and stored in computer memory. In the same manner, the system also knows where the critical display area is or the critical identification area and unpacks this information according to the above-described procedures. The stored information as unpacked is then directed to a digital to analog converter which essentially forms part of the digitizer or may be programmed in the computer. Essentially, the digital information is again transformed into an analog video signal for display on the television monitor and this essentially ends the entire process.

Figure 9:
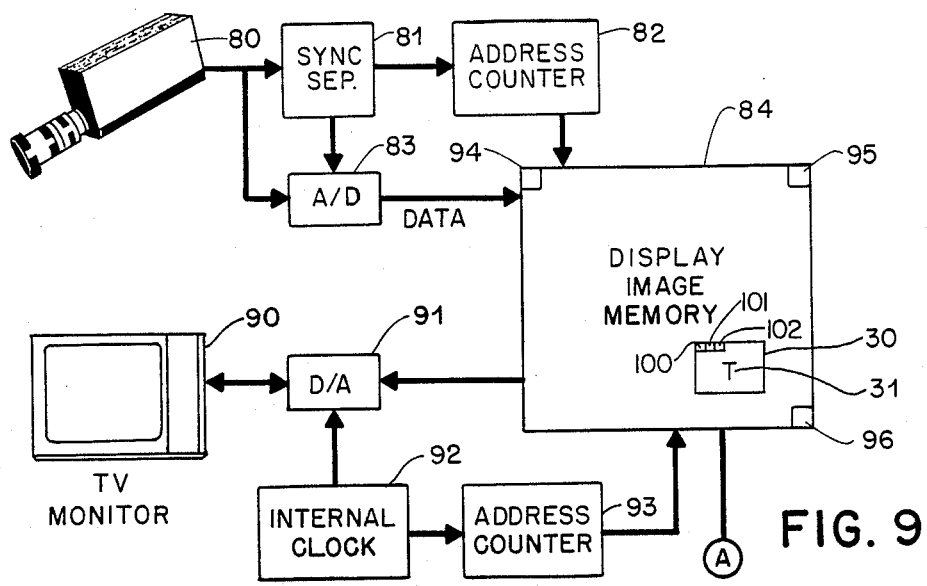
FIG. 9 is a simple block diagram showing the system as implemented to generate the data for the window area and the critical identification area.

Referring to FIG. 9, there is shown a simple block diagram indicative of system operation. Essentially, the television camera 80 produces at its output an analog television signal. The signal typically contains horizontal and vertical sync. These sync components are separated from the television signal by means of a sync separator 81. The sync separator 81 is a conventional component and is well known in the television art as how to separate or strip horizontal and vertical sync from the television signal. The horizontal and vertical sync as stripped from the video input signal are used to generate a clock for the analog to digital converter 83 and an address counter clock for the address counter 82. The analog to digital converter is employed to convert the television signal to digital data. As indicated above, such analog to digital converters 83 are well known in the art and many examples of suitable components which will operate to convert a video signal into a digital signal are well known. Essentially, the output of the analog to digital converter 83 is entered into a display image memory 84 which is sequentially addressed by means of the address counter 82. In this manner, data indicative of the digitized video information is entered and stored in the memory at appropriate locations. Each analog to digital conversion is called a pixel and is represented as an 8 bit byte having 256 pixels across ×256 pixels down. In any event, certain analog ot digital converters employ a mode called a non-interlace mode whereby the effective output is 256 pixels across ×240 pixels down. It is immediately understood that the system can accommodate any such digitizer, including those digitizers which employ 512 pixels ×512 pixels.

The display image memory 84 contains the entire video field. The top left corner 94 representing address 0, the top right corner 94 representing the address 255, and the lower right corner 96 represents the last address with a pixel value of 0 equal to black and a pixel value of 255 equal to white. An internal clock 92 generates the clock signal for the digital to analog converter 91 and for the address counter 93. These components are used to read the contents of the display image memory 84 and to convert those contents back from digital to analog for display or redisplay on a television monitor 90 which is included for operator viewing. After each full video image is converted into digital form and stored in the image memory 84, a pixel value of 255 which is full white is written into the image memory forming a white box or window 30 identifying to the operator the area that will be packed and stored onto the magnetic card.

It is of course expressly understood that the window 30 can appear anywhere on the video display. Essentially, as one will ascertain, the window which is generally rectangular or square in shape has four distinct corners which can be represented in terms of pixel positions to determine the horizontal width. The vertical dimension consists of a definite number of lines. Hence, by the use of a pixel counter and a line counter one can accurately position the window 30 on the face of the video display. It is of course, understood that by such pixel counting and line counting techniques, one can place the window on the face of the television monitor in any position desired. In addition, the T 31 which is indicative of the critical identification area, is also written within the window. The T as indicated above identifies the CIA which is used to align the eyes, nose and mouth of the subject. It is the critical area that enables positive identification of a person or an object. the remaining window is used as a reference data and does not require refined detail. When the window is impressed onto a storage device, the critical area will contain twice as much data which produces a very close representation of the original image such as the face of the person. This additional data enables accurate authentication of the person's face as well as enabling one to recognize each individual based on the data which is stored on the magnetic stripe associated with a credit card.

The process of analog to digital conversion and digital to analog conversion utilizing the window 31 and the T shaped critical identification area is displayed together with the television image of the individual until approval is indicated by the operator. After such approval, the window reference data is removed from the window area of the memory and packed into a suitable buffer. The address of the first pixel 100 of the window is the upper left hand corner of the window. As explained above, the window 30 consists of 68 pixels across ×108 lines and can be positioned anywhere. Hence, each pixel as 100 is then directed to a buffer. The operation to be explained is simply implemented by means of conventional shift registers or by means of conventional programming techniques. As one will understand from the description to be given, the data to be stored is generated by the transfer of suitable bits from one byte to another byte. Essentially, one forms a packed pixel which consists of 8 bits. Four of the bits are indicative of one pixel value, while the remaining four bits are indicative of an alternate pixel value. In this manner, one is able to store the intensity of two alternate pixels in a single 8 bit number.

Figure 10:
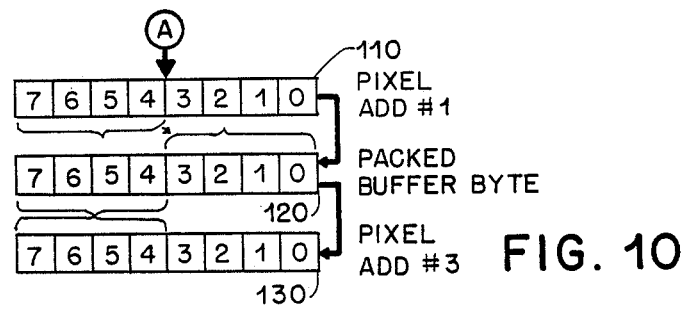
FIG. 10 is a system diagram showing the necessary components for generating and reading data from a credit card.

As one can understand, the display image memory 84 contains all pixels indicative of the television picture. This data is packed into the window area. What occurs now is after data has been received from the memory, the data indicative of the window area 30 is moved into a buffer according to the following sequence. The first byte 100, which is indicative of data within the window area 30 is moved into a buffer 110. This byte consists of 8 bits designated as 0 to 7. The upper four bits of the first byte are moved into the lower four bits of a storage byte indicative of storage register 120. The system then skips byte 2 in the window area or skips pixel 101. The next pixel which is pixel 102 is then removed and stored into register 130. For purposes of convenience, registers 110 and 130 are shown separately, but it is understood that the same register can be employed. Hence, one now removes the byte 102 from the window memory and moves the upper four bits of this byte which is the third byte into the upper four bits of the first packed byte in register 120 as indicated for example in FIG. 10 which shows registers 110, 120 and 130. It is of course understood that the means for clocking the registers and so on are conventional and are well known in the art. Then the system operates to skip the next window byte and goes to remove the next odd byte from the window. Again, the four upper bits of this byte are moved into the four lower bits of the next buffer byte.

Thus, according to the above, the next window byte is then skipped and the following window byte is removed from memory where again the four upper bits are placed into the four lower bits of a packed buffer. This process continues until a complete television line is finished. When a line in the window area is finished, the system now proceeds to skip the next even window line. In this manner, the window address is set to the beginning of the next odd line and the above-noted steps are continued until that line is finished. Hence, the system operates to skip pixels and to skip lines. This effectively compresses the field within the window area which transforms the 68 pixels by 108 lines into an effective storage of 32 pixels by 54 lines.

The next step in the process is to remove the first byte from the critical identification area as manifested by the T zone 31. It is again understood that the T zone 31 is accurately defined with regard to the window and hence can also be defined by a beginning pixel, an end pixel and encompassing a given number of horizontal lines. The critical identification area may be a few pixels wide resulting in a block T form rather than a single line. Thus, one then removes the first byte from the critical identification area. The address of the first byte will be on an odd window line which is the same as the window data, but this byte would be an even byte. All even bytes were previously skipped during the window scan as described above. Hence, this first byte indicative of the critical identification area is again packed as described above where the upper four bits of the byte are moved into the lower four bits of the next buffer byte. The system then skips the next odd window byte. The reason for this is that the next odd window byte was already responded to during the scanning of the window area. The system then operates to remove the next even byte from the critical identification area where upon the upper four bits of this byte are moved into the upper four bits of the same buffer byte. The system then skips the next odd window byte as this was scanned during the scanning of the window area and proceeds to remove the next even byte from the critical identification area storage where again the upper four bits are moved into the lower four bits of the next buffer byte. The process is continued until a line is finished. Then the system skips the next window line which again was responded to during the scan of the window area. The system sets the critical area address to the beginning of the current odd line and the steps as indicated above are repeated until the critical area has been responded to.

Figure 11:
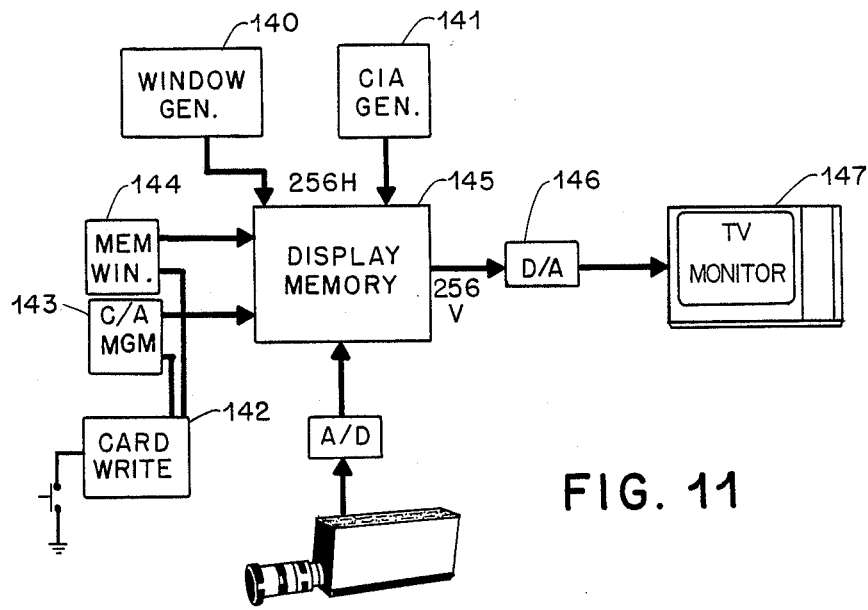
FIG. 11 is a system diagram showing the entire system.

Now that one has gained an understanding of how the window and critical identification area data are developed and how the respective bits are packed in those areas, reference is now made to FIG. 11, which shows a block diagram representation of the entire system. Essentially as seen from FIG. 11, the display memory is associated with a window generator 140 and a critical identification area generator 141. As explained above, the structure of the window generator as 140 and a critical identification area generator as 141 should be completely obvious to those skilled in the art. As indicated, one knows exactly the horizontal and vertical dimensions of the window in terms of pixels and in regard to lines. In a similar manner, one knows exactly where the critical identification area is with respect to the window. Hence, the function of the window generator 140 is to generate the pixel and horizontal line value for the entire rectangular or square area which encompasses the window 30. The function of the CIA generator 141 is to generate the T zone in regard also to the appropriate pixels and as well as the suitable horizontal lines.

As indicated above, the data generated in regard to the window area and in regard to the critical identification area are inputted as bytes to a credit card where this data is impressed upon a magnetic stripe or other memory associated with a credit card. As seen in FIG. 11, there is shown a card reader 142. The card reader or writer is a conventional unit many of which are available from many different sources. Essentially, such readers will respond to magnetic data impressed upon a magnetic stripe of a card to produce at an output during a read mode various digital data on the stripe. As seen from FIG. 11, the sequence for reading a card is relatively simple. The card is read and the data is impressed on a CIA memory 143 and a window memory 144. Essentially, the data is stored in the memories exactly as explained above. The data then stored is entered into the display memory or a separate memory of a computer 145 where it is aligned strictly according to the above-noted techniques. The data is then outputted from memory 145 via a digital to analog converter 146 where it is then displayed upon the video monitor 147 within the window area. In any event, when the data on the magnetic card is read, the display does not display the T zone, but includes the higher density data indicative of the critical identification area, thus enabling one to recognize the person who is the card holder or the rightful possessor of the magnetic card. Essentially, the process of reading a card involves moving the data from the window area into a buffer and removing the data from the buffer according to the manner in which it was coded. For example, to implement reading the card, a byte is removed from the buffered area. The buffer can be a register or a memory, then one moves the lower four bits of the buffer byte into the upper four bits of an odd window byte. One then skips the next even window byte. Then one moves the upper four bits of the same buffer byte into the upper four bits of the current odd window byte, then one skips the next even window byte. These processes are continued until a complete line is finished. Then one skips the next even window line and the window address is set to the beginning of the current odd line. Then the above-noted steps are implemented until the entire window is processed on the alternate line and pixel basis. Hence, for each line one removes the next byte from the buffer area, moves the lower four bits of the buffer byte into the upper four bits of the odd window byte, then skips the next even window byte, then moves the upper four bits of the same buffer byte into the upper four bits of the current odd window byte and this process continues on a alternate line basis until all the data associated with the window area 30 is impressed upon the monitor. Then one moves into the critical area storage such as memory 143. In the critical area, one then removes the next byte from the buffer area, moves the lower four bits of this buffered byte into the upper four bits of even critical area bytes. One then skips the next off window byte. This is skipped because this byte was accomplished and accounted for during the window scan. Then one moves the upper four bits of the same buffer byte into the upper four bits of the current even window byte then one skips the next odd window byte. This process is continued on a alternate line basis until each line is finished. Then one skips the next even window line. The reason why the next even window line is skipped is because this line was scanned during the window scan. One then sets the critical area address to the beginning of the current odd line and the packing and the unpacking of bits continues as described above until the critical identification area is finished. Essentially, this procedure completes both the packing and unpacking of the window data as well as the critical identification area data.

As indicated above, the data is superimposed upon one another whereby the higher packed data of the critical identification area enables one to accurately portray the video image of a particular individual to enable that individual to be authenticated or recognized.

Based on the above description, it is of course understood that one need not provide separate memories or separate scans for the window area as compared to the critical identification area. This should be immediately apparent to those skilled in the art. As indicated above, the window area is definiately defined by means of a first value pixel and a last value pixel which essentially defines the horizontal width of the window. The vertical width of the window is defined by the number of lines that the window accommodates. The critical identification area in a similar manner is also defined due to the fact that it commences at a given line within the window area and at a given pixel value and hence the dimensions of the critical identification area are also known. Thus, one has the complete addresses for both the window and critical identification area. Hence, the system can operate to simultaneously process data in the window area and the critical indentification area by implementing the above-noted procedure. Thus, accordingly, when one commences a window scan, one does not have to skip alternate pixels and alternate lines throughout. In any event, when one now encounters the first pixel of the critical identification area, one then commences to implement the above-described procedure for the critical indentification area wherein all pixels that would be skipped during the normal window scan are now filled in during the critical identification scan or all pixels are responded to during the critical identification scan as well as all lines are responded to during this scan. Hence, one will produce in a single scan different data for the window area outside the critical identification area and will produce more accurate data during the scanning of the critical identification area.

It should be obvious from the above that there are numerous way of implementing the techniques described. It should also be obvious that the above system results in a substantial compression of data due to the fact that one selects a critical identification area which is indicative of the main recognizable aspects of the particular object to be authenticated or whose image is to be displayed. In the case of the human being, the most critical areas involve the eyes, nose and mouth area of the individual. Hence, in this manner this system produces more exact data in regard to the critical identification area then it does for the remaining data which encompasses the remainder of the person's face such as the forehead, the hairline and so on. It has been definitely ascertained that by the use of this video compression technique, one can provide accurate and truly representative displays of persons enabling those persons to be directly recognized from the data displayed on the television monitor. This data of course is impressed on a magnetic stripe associated with a credit card or any other limited storage means. The system thus enables one to place a person's electronic image on a magnetic stripe associated with a credit card. As one will ascertain, the applications of such a system inherent in the ability to provide such information are numerous. Hence, the resultant credit card can be utilized for all purposes such as bank identification, security identification, credit card identification and a various other applications too numerous to mention. It is a major aspect of the present invention to provide a simple means whereby a minimum number of bytes can be impressed upon a limited storage medium enabling one to therefore display a accurate image of a person or object to be authenticated.

Many other examples and structures will become obvious to those skilled in the art when reading the above-noted specification and hence the appended claims are demmed to be indicative of the inventive concepts described above.

What is claimed is:

1. A system for storing an image of an object to be identified to enable said image to be retrieved for display on a display screen area comprising:
   scanning means for scanning said object on a line-to-line basis in a vertical direction to provide analog information for each of said lines indicate of the information content of the image of said object to enable said object to be displayed on said display screen area;
   digitizing means for converting said analog information into digital information for each of said lines to provide a given number of pixels for each line, with each pixel indicative of area information content along said one associated line;

means for generating a window area within said display screen area and for packing said window area with a first set of limited digital information for a given set of lines and pixels within said window area as derived from said digital information wherein said window area contains information content of said object of a reduced number of pixels and of a reduced number of lines;

means for generating a critical identification area within said window area with said critical identification area selected according to information content in said object which distinguishes said object from other like objects and for packing said critical identification area with a second set of limited digital information for lines and pixels within said critical identification area as derived from said digital information and wherein said second set of digital information of said object is indicative of information content for pixels and lines not within said first set; and means, responsive to said first and second sets of digital information, for causing storage of the first and second sets of digitized information on a storage medium.

2. The system according to claim 1, wherein said scanning means includes a television camera for providing a video signal of a given number of lines indicative of the information content of said object.

3. The system according to claim 2, wherein said given number of lines is 256 lines.

4. The system according to claim 3, wherein said digitizing means provides 256 pixels for each of said lines.

5. The system according to claim 1, wherein said first set of digital information for a given set of lines and pixels includes that information within said window area for every other pixel on a line and for every other line within said window area as derived from said digital information from said digitizing means.

6. The system according to claim 5, wherein said second set of digital information within said critical identification area includes that information skipped by said means for generating said window area, whereby said second set of information includes pixels skipped by said window area means and lines skipped by said window area means.

7. The system according to claim 6, wherein said window area includes at least 68 pixels in the horizontal direction by 108 lines in the vertical direction.

8. The system according to claim 7, wherein every other pixel is skipped in the horizontal direction by said means for generating said window area to provide effectively 34 pixels in the horizontal direction, and every other line is skipped by said means for generating said window area to provide effectively 54 lines of information in the vertical direction.

9. The system according to claim 1, wherein said object is a person's face.

10. The system according to claim 9, wherein said critical identification area includes those image areas primarily occupied by the eyes, nose and mouth of said person.

11. The system according to claim 10, wherein said critical identification area is a "T" shaped area with the top horizontal arm of said "T" directed along a line common to the eye area of said person, with the vertical arm of said "T" directed along a line common to the nose and mouth area of said person.

12. The system according to claim 1, wherein said storage medium is a magnetic stripe associated with a credit card.

13. The system according to claim 1, wherein said first set of information of said window area includes a plurality of digital words each of a given bit length with a first group of bits indicative of the value of a first pixel and a second group of bits indicative of the value of a second pixel, each associated with the same line.

14. The system according to claim 13, wherein said given bit length is eight bits, with said first and second pixels being four bits each.

15. The system according to claim 1, further including display playback means responsive to said stored digital information for providing a display of said object according to said first and second sets of digital information.

16. A method for storing an image of an object to be identified and to enable said image to be retrieved and displayed, comprising the steps of:

scanning said object on a line-to-line basis to provide an analog information signal for each of said lines indicative of the information content of the image of said object;

converting said analog information to digital information for each of said lines to provide a given number of pixels for each line, with each pixel indicative of eare information content along said one associated line;

generating a window area of a given number of pixels in a horizontal direction and a given number of lines in a vertical direction;

packing said window area with selected pixels indicative of a first set of converted digital information;

generating a critical identification area within said window area indicative of areas of said object which mainly distinguish said object from other like objects;

packing said critical identification area with a second set of converted digital information indicative of pixels not selected in said first set;

storing said first and second sets of converted digital information on a storage medium.

17. The method according to claim 16, wherein the step of scanning includes scanning said object with a television camera to provide a video signal consisting of a given number of television lines.

18. The method according to claim 17, wherein the step of converting said analog information includes digitizing said video signal on a line-to-line basis to provide a given number of pixels each of a given bit length for each of said video lines, and storing said pixels in a memory whereby a complete image of said object is stored in said memory via said pixels.

19. The method according to claim 18, wherein the step of generating a window area includes generating said area having 68 pixels in a horizontal direction for each line and having 108 lines in the vertical direction.

20. The method according to claim 16, wherein the step of packing said window area includes packing said window area with every other pixel along selected lines, with said selected lines being every other line.

21. The method according to claim 16, wherein said object scanned is a person's face.

22. The method according to claim 21, wherein said step of generating said critical identification area includes generating a pattern encompassing the eyes, nose and mouth area of said person's face.

23. The method according to claim 20, wherein the step of packing said critical identification area includes packing said area with pixels and lines not included within said window area.

24. The method according to claim 22, wherein said pattern is a "T" like pattern with the horizontal top arm of said "T" directed along a common line along the eyes of the image of said person, with said vertical arm of said "T" directed along a common line along the nose and mouth area of the image of said person.

25. The method according to claim 16, wherein the step of storing said first and second sets of converted digital information includes storing said information on a magnetic stripe associated with a credit card.

26. The method according to claim 16, further including the step of:
generating said first set of digital information by forming packed pixels from said given number of pixels with each packed pixel of the same bit length as said pixels in said given number, with a first group of bits indicative of the information content of one pixel in said given number and a second group of bits indicative of the information content of an alternate pixel in said given number.

27. A system for storing an image of an object to be identified to enable said image to be retrieved for display on a display screen, comprising:
first means responsive to said object for forming a given number of pixels indicative of the information content in said object;
means for generating a window area on said display screen and for packing said window area with certain selected ones of said pixels indicative of first information relating to the image of said object;
means for generating a critical identification area within said window area, said critical identification area indicative of portions of said object which tend to distinguish said object from other like objects, and for packing said critical identification area with other different selected pixels indicative of second information relating to the image of said object with the critical area having a higher resolution than the window area; and
means, responsive to the means for generating a window area and the means for generating a critical identification area, for storing pixels indicative of the first and second information.

28. A limited storage medium for use in a system enabling recognition of a face of a person by storing a digital image of the face on the medium and reading the stored image from the medium and displaying the stored image to permit recognition of the face comprising:
a stored first digital data in the storage medium indicative of first information content of said face within a selected area on a display screen at a first resolution; and
stored second digital data in the storage medium indicative of a second information content within a critical area encompassed within said selected area at a second resolution greater than the first resolution to permit recognition of said face upon reading and displaying of the stored first and second stored digital data.

29. The system according to claim 28, wherein said limited storage medium is a magnetic strip associated with a credit card.

* * * * *